United States Patent [19]
Cohn et al.

[11] Patent Number: 5,791,231
[45] Date of Patent: Aug. 11, 1998

[54] SURGICAL ROBOTIC SYSTEM AND HYDRAULIC ACTUATOR THEREFOR

[75] Inventors: Michael B. Cohn, San Francisco, Calif.; D. Curtis Deno, Missouri City, Tex.; Jennifer T. Fujii, Sunnyvale, Calif.

[73] Assignee: Endorobotics Corporation, Warren, N.J.

[21] Appl. No.: 62,400

[22] Filed: May 17, 1993

[51] Int. Cl.$^6$ .................................. F01B 29/00
[52] U.S. Cl. .................. 92/88; 92/128; 92/177; 606/1
[58] Field of Search .............. 92/121, 128, 177, 92/76, 88; 606/1; 128/898; 395/80, 86, 97; 901/14, 15, 28, 29, 36, 37

[56] References Cited

U.S. PATENT DOCUMENTS

| | | | |
|---|---|---|---|
| 4,267,758 | 5/1981 | Muhr et al. | 92/172 |
| 4,763,669 | 8/1988 | Jaeger . | |
| 4,848,338 | 7/1989 | DeSatnick et al. . | |
| 4,988,981 | 1/1991 | Zimmerman et al. | 340/709 |
| 5,142,930 | 9/1992 | Allen et al. | 74/469 |

OTHER PUBLICATIONS

Fisher, "Telepresence master glove . . . effectors", SPIE, vol. 725, Intelligent Robots . . . (1986), pp. 396–401.

Scott S. Fisher, "Telepresence master glove controller for dexterous robotic end–effectors", SPIE, vol. 725, Intelligent Robots and Computer Vision: Fifth in a Series (1986), pp. 396–401.

*Primary Examiner*—Michael Peffley
*Attorney, Agent, or Firm*—Foley & Lardner

[57] ABSTRACT

A hydraulic actuator is described which has a layered structure and a flattened piston assembly to enhance production speed and reduce the costs of assembly. A system for performing surgery is also described incorporating the hydraulic actuator, having a sensory glove, a computer, and a slender robot manipulator which can be inserted into the human body through a small incision. The robot manipulator has a layered structure with integrated hydraulic pistons. This design allows the use of a novel manufacturing process in which all of the parts are formed from laminated sheets of material. Seals are formed to prevent leakage of hydraulic fluid by introducing castable rubber into enclosed channels in the structure.

14 Claims, 5 Drawing Sheets

SURGICAL ROBOTIC SYSTEM AND HYDRAULIC ACTUATOR THEREFOR

FIELD OF THE INVENTION

This invention relates to hydraulic actuators having a layered structure useful in robots, particularly in multi-jointed surgical instruments which may be employed in laparoscopic surgery.

BACKGROUND

Laparoscopy is a well known technique for examining the peritoneal cavity. A long, rigid endoscope (laparoscope) equipped with a sheath (trocar) is employed. The abdominal wall is punctured and a pneumoperitoneum is induced to distend the abdomen. The trocar is inserted into the puncture, and the laparoscope introduced through the trocar into the peritoneal cavity. Laparoscopic surgery is performed using forceps, staplers, or microscissors introduced through additional punctures. These instruments are long and slender, to allow passage through the small aperture afforded by the puncture. Using these instruments, the surgeon can perform operations such as removal of the gall bladder.

Identical equipment is employed in thoracoscopic surgery to effect examination and surgical treatment of structures in the chest cavity.

Laparoscopic surgical instruments are similar to conventional surgical instruments in function, but are typically long and narrow to allow insertion through a 5–12 millimeter incision. Such forceps can be used for applying traction to tissues or for suturing. Unfortunately, the length of the instrument makes fine manipulation awkward. Also, since the abdominal wall is essentially rigid, the instrument: acts like a lever, with its fulcrum at the point where it penetrates the wall. Thus, the instrument's tip moves in a direction opposite that of the surgeon's hand on the instrument handle. This disrupts eye-hand coordination. Additionally, unlike a human arm, the instrument lacks joints. For this reason, fine motions are difficult to execute, and surgical tasks become awkward, time-consuming, and sometimes risky.

Some instruments are available with a joint (e.g., U.S. Pat. No. 4,763,669 to Jaeger, 1988) but the control for the joint's motion is in a different location than that for the jaw action. Thus, coordinated motion for tasks such as suturing is not enabled.

To address these problems, a robotic surgery system, including a master and a slave has been suggested. See Green et al., Telepresence: Advanced Teleoperator Technology for Minimally-invasive Surgery, *Medicine Meets Virtual Reality*, UCSD, San Diego, Jun. 4–7, 1992. The master has several control handles which the surgeon can grasp and manipulate, much like the handles of ordinary surgical instruments such as forceps and scissors. These control handles are affixed to a system of electronic sensors and motors. The slave is an arm-like manipulator equipped with a conventional laparoscopic instrument (e.g., forceps). The master and slave are linked by a computer in such a way that the surgeon can manipulate the slave instrument with natural, coordinated motions of his hands, just as if he were using a conventional surgical instrument. Also, forces encountered by the slave instrument are sensed by force sensors in the slave robot and reflected back to the surgeon through the motors in the master. All of these features make laparoscopic surgery easier and faster. Nevertheless, this system is fundamentally limited by the fact that the surgical instrument used by the slave robot is the same as that used originally by the laparoscopic surgeon: no additional joint is present. Moreover, this system's complexity may make it impractical for use in the operating room. Additionally, the system's parts are nondisposable, making sterilization difficult. Finally, the system is extremely expensive.

Fisher (SPIE Vol 726 Intelligent Robots and Computer Vision, 1986; see also U.S. Pat. No. 4,988,981 to Zimmerman, et. al. 1991) describes a glove with sensors for recording and transmitting the positions of the wearer's hand and fingers in real time to a computer. Applications are suggested, including a system to let an earth-based surgeon operate on a patient in orbit. The system would include sensory gloves worn by the surgeon, and robotic manipulators in the orbital environment. The manipulators would be anthropomorphic in size and shape, able to grasp and manipulate instruments such as scalpels and forceps under the surgeon's control.

In practice, unfortunately, such a system does not seem workable. If the surgeon is not physically present at the patient's location, his ability to respond to complications is severely hampered. For instance, the patient may require defibrillation or CPR. In the event of arterial bleeding, the surgeon may need to find and stop the bleeding within seconds. Implementation of such a system, with a robot manipulator capable of such diverse tasks, seems prohibitively expensive, if not beyond current technology. Even if implemented, the benefit of separating surgeon and patient is not apparent, since a typical surgery requires a team of trained workers, as well specialized facilities.

Moreover, conventional hydraulic actuators such as cylinders are not practicable in surgical instruments. They require precisely fabricated parts, especially to avoid leakage. This makes the actuators expensive. Moreover, were one to simply miniaturize an existing actuator, it would be extremely difficult to maintain the requisite precision. Finally, hydraulic connectors are expensive and bulky.

Presently, the surgeon must break bones and sever muscles to access structures such as the heart, lungs, and brain. Complications often result. The present invention allows the surgeon to access the inside of the body without inflicting damage and without any impediment to manual dexterity or speed.

It is an object of the present invention to provide a system that does not merely make surgery more convenient, but which enables entirely new surgical procedures that were hitherto impossible. This is made possible by a uniquely designed hydraulic actuator having a layered planar structure. The layered planar structure of the hydraulic actuator according to the present invention is advantageous because the parts can be cut from a single laminated sheet and the seals can be formed in-situ. This permits rapid production at a fraction of the cost of conventional hydraulic actuators. Moreover, the actuator can be easily miniaturized and made from light-weight materials, unlike conventional hydraulic actuators.

DETAILED DESCRIPTION OF THE INVENTION

The present inventors have discovered a uniquely structured hydraulic actuator of sufficiently small dimensions, yet with enough power, to be useful in surgical instruments. Moreover, the actuator of the present invention is inexpensively and rapidly produced.

In one embodiment, the present invention comprises a layered hydraulic actuator comprising a top plate, a middle plate, a bottom plate and a piston having a head and a shaft. The piston shaft optionally preferably has a rectangular cross-section as this design is easy to produce. However, beveled edges may also be used or any other type of cross-section provided that it is uniformly maintained down the length of the shaft so that the collar-seal maintains contact.

The middle plate comprises at least one chamber which houses the piston. Preferably, there are two chambers. The first chamber has two ends and is adapted to receive the head of the piston and permit the piston head to move up and down the length of the first chamber between the two ends. The first chamber is joined by its first end to a second chamber which is adapted to receive the shaft of the piston. Means for preventing the piston head from passing into the second chamber are included at the junction of the two chambers. For example, the means for preventing the piston head from passing into the second chamber can simply be a pair of inwardly facing tabs positioned at the juncture of the two chambers.

The actuator further comprises means for conducting hydraulic fluid into the piston chamber. Preferably, the middle plate comprises at least one channel which is capable of conducting hydraulic fluid from the edge of the middle plate to the piston chamber or first chamber (if two chambers are used). More preferably, there are two channels which permit the flow of hydraulic fluid and which originate at an edge of the middle plate, one channel connecting to the first end of the first chamber and the other channel connecting to the second end of the first chamber. Alternatively, flexible tubing may be used as the means for conducting hydraulic fluid.

The top plate and the bottom plate are attached to the top and bottom, respectively, of the middle plate, thereby enclosing the first and second chambers containing the piston. optionally, a single plate may be substituted in place of separate bottom and middle plates. In this embodiment, there are only two plates, i.e., the top and bottom plates.

In another embodiment, the present invention is directed to an apparatus for performing surgery comprising a surgical instrument, a sensory glove, and computer means for connecting said sensory glove to said surgical instrument which translates the motion detected by the sensory glove into a command that causes the surgical instrument to mimic the detected motion of the wearer's hand.

Preferably, the apparatus for performing surgery comprises (a) an arm with at least one joint and one end fitted with an end-effector which is actuated by at least one actuator as described herein;

(b) a sensory glove for sensing motion of the wearer's hand; and (c) computer means for connecting said glove to said arm which translates the motion detected by the sensory glove into a command that causes the end-effector and said at least one joint to mimic the detected motion of the wearer's hand.

Preferably, the actuator is selected from the group consisting of externally driven cables, shape memory alloy, pneumatic actuators, electric motor actuators, ultrasonic motors, and wobble motors. More preferably, the actuator is a hydraulic actuator as defined above.

Preferably, the surgical apparatus of the present invention further comprises a rotary bearing which permits the arm to rotate and a rotary position sensor for detecting the relative rotation of the arm.

The end-effector of the surgical apparatus may be a blunt dissection probe, a stapler, a pair of forceps, needle holders, a laser dissection instrument, cutters, or grasping means such as a pair of jaws, or any other end-effector known in the art.

In another embodiment, the present invention is directed to a manipulator having at least one joint and comprising substantially planar components, said components (a) lying in a plane containing the length of said arm when the arm is fully extended, (b) lying in parallel layers, (c) having among them at least one groove for conducting hydraulic fluid, (d) incorporating at least one hydraulic actuator for imparting motion to at least one of said joints, whereby said manipulator is economically manufactured by forming the components for each layer of the manipulator from a sheet of material, then joining the several sheets in a stacked arrangement to form the finished manipulator.

In another embodiment, the present invention is a method of producing a layered hydraulic actuator comprising the steps of (a) forming top, bottom, and middle plates, wherein the middle plate has a cut-out first chamber and an adjoining second smaller chamber, (b) inserting a piston having a head and a shaft into the chambers of the middle plate such that it can slide back and forth within the chambers, (c) forming channels in the middle plate to conduct fluid into said cutout, and (d) joining said lower, middle, and upper plates in a stacked arrangement, such that the chambers of the middle plate are enclosed to form a cavity containing the piston.

Optionally, this method further comprises the steps of (e) forming grooves in said upper, middle, and lower plates, in a configuration which circumscribes said first chamber and said channels, (f) filling said grooves with a fluid, (g) assembling said actuator, and (h) causing said fluid to solidify, whereby the solidified fluid provides a seal to prevent leakage of hydraulic fluid, especially in cases where said actuators are extremely small or must be produced at low cost.

In a similar way, a collar-seal may be advantageously formed in-situ at the junction between the first and second chambers which surrounds the piston shaft and prevents the leakage of fluid from the first chamber into the second chamber. This can be accomplished by forming slots near the junction of the first and second chambers that run perpendicular to the direction of the piston shaft. The slots, in combination with channels in the top and bottom plates, form a ring around the piston shaft. When a seal-forming liquid is introduced therein, a collar-seal is formed which is contiguous with the material forming the upper and lower gaskets described below.

Preferably, the fluids which form the seal and gaskets of the present invention are castable rubbers, e.g., silicone rubber, and other seal-forming fluids known in the art such as teflon coatings, FLEXANE™ (produced by Du Pont, Inc.), and those available for other rubber casting techniques.

In another preferred embodiment, the piston residing in the piston chamber is provided with a piston ring formed by introducing a liquid into said chamber and causing said liquid to solidify, whereby the piston ring forms an effective seal between the piston and chamber walls.

In another preferred embodiment of the method of producing the layered hydraulic actuator, a gasket is provided to prevent the leakage of fluid between the plates through the slots at the juncture of the first and second chambers, wherein the gasket is formed by the steps of:

(a) providing grooves in the top and bottom plates which circumscribe the slots and channels of the middle plate, (b) introducing a liquid into said grooves, (c) assembling said actuator, and (d) causing said liquid to solidify.

In order to custom fit the piston to the chambers of the middle plate, the method for producing the hydraulic actuator may also comprise the steps of:

(a) coating said piston with a liquid, (b) inserting said piston into said piston chamber, (c) causing said liquid to solidify, whereby a high-quality seal may be formed around the piston to the walls of said chamber in a precise manner enabling the piston to slide within the piston chamber with low friction.

Preferably, the hydraulic actuator of the present invention is of minimal size in order to minimize the overall size of the surgical instruments in which it is embodied. This, in turn, minimizes the size of the incision through which the instrument is inserted into the body. In this embodiment, the hydraulic actuator of the present invention is no more than 3 centimeters in width and no more than 5 centimeters in length, so as to pass through a small incision and fit the dimensions of the peritoneal cavity. The actuator of this embodiment produces a force of at least about 4 kilograms and a displacement of at least about one-half centimeter.

The seals and gaskets of the present invention are advantageously formed in-situ. However, they may be separately produced by conventional molding techniques and then inserted into the actuators during assembly. If the seals are separately manufactured, materials such as Buna-N, teflon, or a combination thereof may be used.

The actuator and robotic systems of the present invention can be used in a variety of different ways, not only in laparascopic surgery, but also in thoracoscopic surgery, which employs instruments similar to those used in laparascopic surgery, for treatment of the chest. Also, they may be used in arthroscopic surgery in which miniature instruments are inserted into the joints. Similarly, they may be used in endoscopic surgery, which utilizes long, flexible tubes inserted into the gut through which various instruments are introduced. Also, they may be used in atheroscopic surgery, which employs flexible catheters through which arterial lumen may be visualized and surgically treated. Endoscopic techniques have also been successfully applied in neurologic and plastic surgery.

The specific techniques used to manufacture the components of the present invention include etching, stamping, molding, photosensitive glass, milling, laser-cutting, waterjet cutting, electrical discharge machine-manufacture, and electroforming.

The present invention is illustrated by, but in no way limited to, the following examples and specific embodiments shown in FIGS. 1-4. In FIGS. 1-4, the reference numbers refer to the following

| | |
|---|---|
| 8 | patient |
| 10 | surgeon |
| 12 | laparoscope |
| 14 | video monitor |
| 16 | sensory glove |
| 18 | microcomputer |
| 20 | manipulator |
| 22 | electrically operated hydraulic valves |
| 24 | base |
| 26 | shoulder joint |
| 28 | elbow joint |
| 30 | forearm |
| 32 | wrist |
| 34 | end-effector |
| 36 | sliding linkage |
| 38 | abdominal wall |
| 40 | hydraulic actuator |
| 46 | fixed jaw |
| 48 | moveable jaw |
| 50 | coupling |
| 52 | upper plate |
| 54 | middle plate |
| 56 | lower plate |
| 58 | slot in upper plate |
| 60 | slot in lower plate |
| 62 | cutout |
| 64 | piston chamber |
| 66 | guide slot |
| 68 | outer oil flow channel |
| 70 | inner oil flow channel |
| 72 | upper gasket channel |
| 74 | uppermost gasket channel |
| 76 | lower gasket channel |
| 78 | lowest gasket channel |
| 80 | piston |
| 82 | head |
| 84 | shaft |
| 86 | piston ring |
| 88 | hole |
| 90 | ferrule |
| 92 | first flexible inlet tube |
| 94 | second flexible inlet tube |
| 96 | gasket |
| 98 | collar seal |
| 100 | pin |

Figure 1:
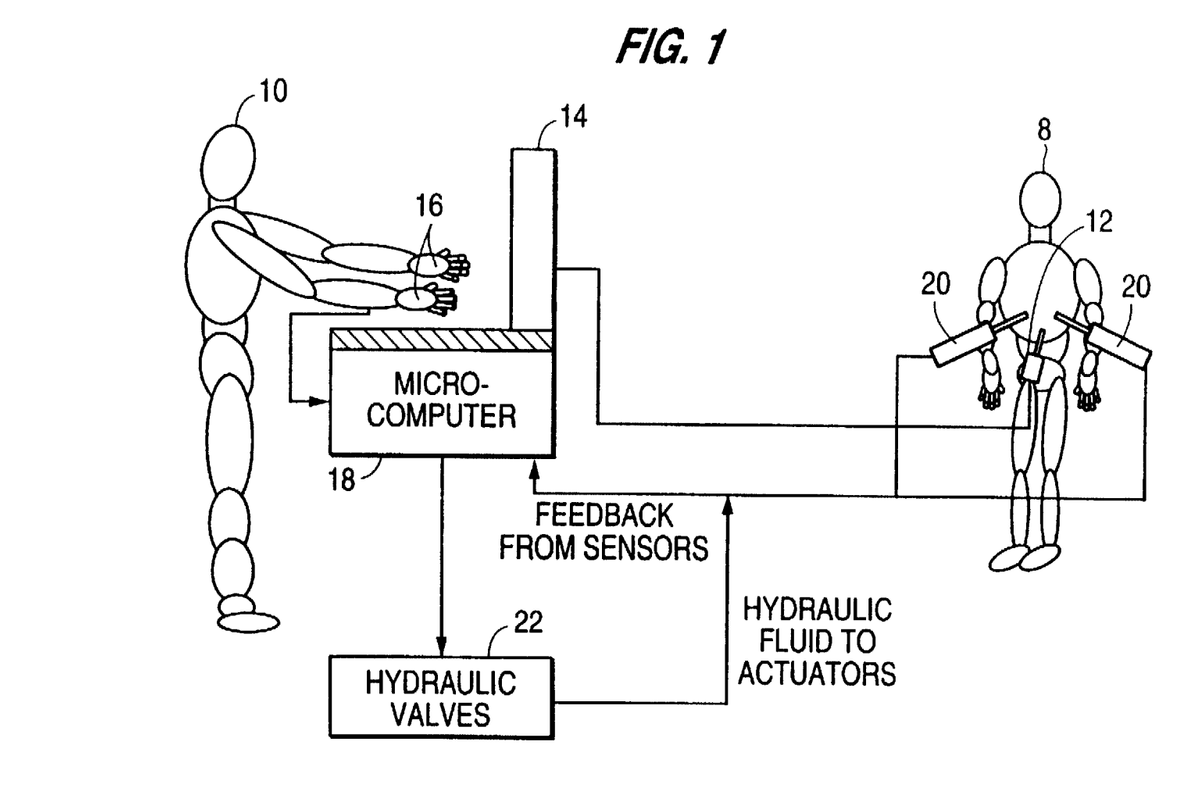
FIG. 1 shows a block diagram of a surgical robot system controlled by a sensory glove.

FIG. 1 shows a block diagram of a typical embodiment of the surgical robot system. The surgeon 10 views the interior of the patient's abdominal cavity by means of a laparoscope 12 and video monitor 14. He wears a sensory glove 16 on each hand. Each glove is able to record the deflection of the thumb and index finger, as well as the spatial position and orientation of the palm, and transmit this information to a microcomputer 18. Microcomputer 18, in turn, controls electrically-operated valves 22. Valves 22 are connected to hydraulic actuators 40 in the joints of manipulators 20.

Figure 2A:
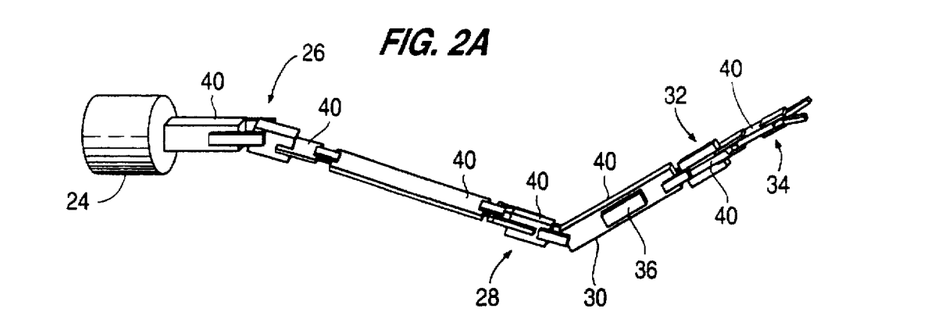
FIG. 2A shows a robotic surgical manipulator incorporating hydraulic actuators to provide motion of the joints.
Figure 2B:
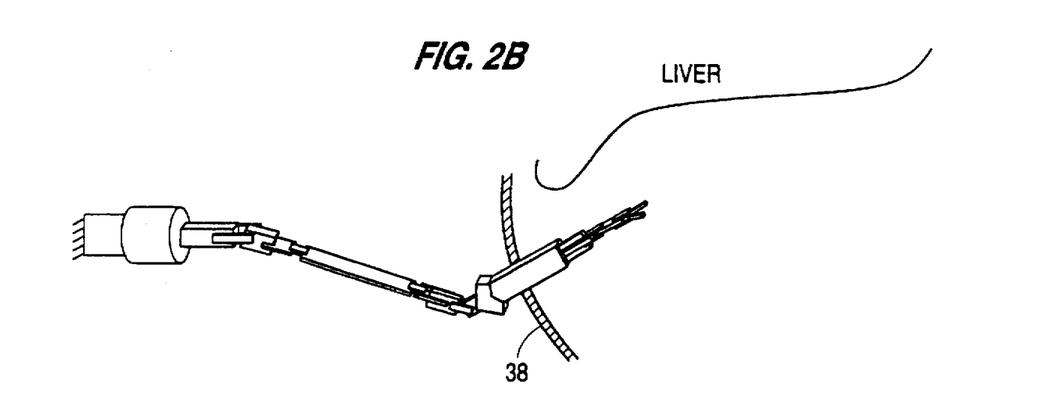
FIG. 2B shows a robotic surgical manipulator incorporating hydraulic actuators to provide motion of the joints extending through an incision.

FIG. 2 shows a detail of surgical robot manipulator 20. Each manipulator comprises a miniature arm with a base 24, shoulder joint 26, elbow 28, forearm 30, wrist 32, and forceps-like end-effector 34. Similar to the human shoulder, shoulder 24 can swivel about two axes: up-down and left-right. These motions are controlled by hydraulic actuators 40. Elbow 28 has the same motions, but is a passive joint without actuators. Forearm 30 has an sliding linkage 36 which is equipped with a hydraulic actuator. Wrist 32 has the same motions as shoulder 24, actuated as in the shoulder. In use, end-effector 34, wrist 32, and most of forearm 30 are inserted through the abdominal wall 38 but the rest of the arm, including base 24, shoulder 26, and elbow 28, remains outside. The base 24 is secured in relation to the operating bed by a clamp. All joints are equipped with sensors for measuring their angle of deflection or degree of extension. Each of the hydraulic actuators is connected to an electrically-operated valve.

Figure 3:
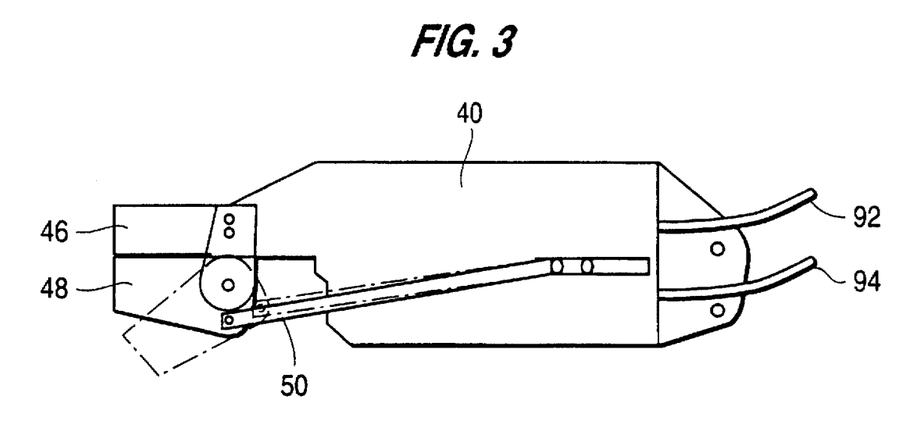
FIG. 3 shows a side view of a robotic gripper incorporating the hydraulic actuator such that it opens and closes a pair of jaws.

FIG. 3 shows a detail of end-effector 34. The end-effector consists of a hydraulic actuator 40, a fixed jaw 46 and a moveable jaw 48. Fixed jaw 46 is fixed with respect to hydraulic actuator 40. The motion output of actuator 40 is coupled to moveable jaw 48 via coupling 50.

FIG. 4 details a typical embodiment of hydraulic actuator 40. The actuator resembles a flattened hydraulic cylinder. It comprises three metal plates: an upper plate 52, a middle plate 54, and a lower plate 56. Upper and lower plates 52, 56 have identically placed slots 58, 60. Middle plate 54 has a cutout 62 roughly in the shape of a spatula. A piston chamber 64 comprises a wide part analogous to the spatula's blade, and a guide slot 66 comprises a narrow part like the spatula's handle. The middle plate 54 has an outer oil flow channel 68 leading from the edge of the plate to the distal end of piston chamber 64. An inner oil flow channel 70 leads from the edge of the plate to the proximal end of the piston chamber.

Figure 4A:
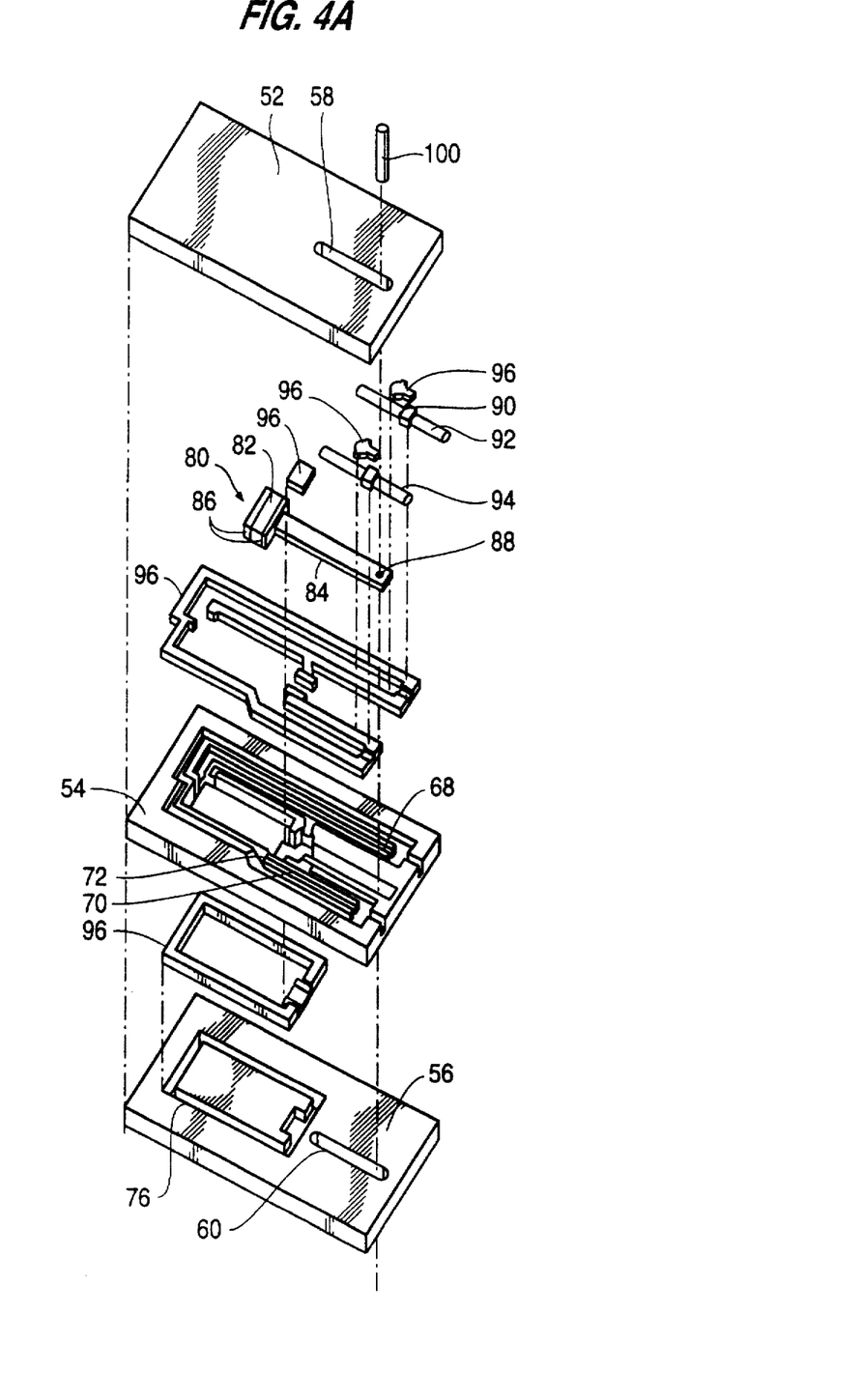
FIG. 4A shows a layered hydraulic actuator with the individual components separated and points of connection indicated by lines.
Figure 4B:
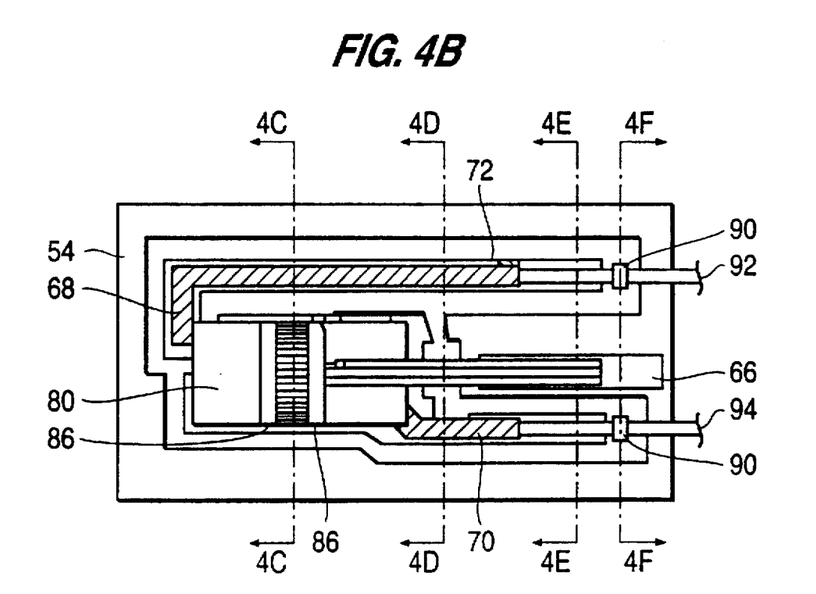
FIG. 4B shows a top view of the middle plate.

An upper gasket channel 72 in the top surface of middle plate 54 circumscribes piston chamber 64 and oil flow channels 68, 70. An uppermost gasket channel 74 in upper plate 52 has a shape identical to that of upper gasket channel 72. A lower gasket channel in the bottom surface of middle plate 54 circumscribes piston chamber 64. A lowest gasket channel 78 in lower plate 56 has a shape identical to that of the lower gasket channel.

A flat T-shaped piston 80 has a head 82 and a shaft 84. Piston 80 has two piston rings 86 of a moldable material ringing its head 82 in a plane perpendicular to its shaft 84. The shaft is provided with a hole 88 at the end. Piston 80 lies flat in cutout 62 and is able to slide back and forth.

A ferrule 90 in the shape of a rectangular block is molded onto a first flexible inlet tube 92, in the configuration of a bead on a string. Tube 92 is inserted partway into outer oil flow channel 68, with its ferrule 90 occupying a widened portioned of the channel. A second flexible inlet tube 94 with a ferrule is likewise inserted in inner flow channel 70.

Figure 4C:
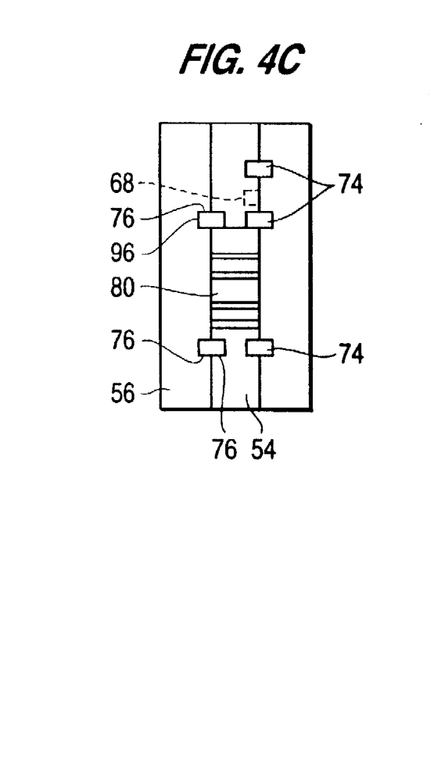
FIG. 4C shows the cross-section through the hydraulic actuator as indicated by the dashed line in FIG. 4B.
Figure 4D:
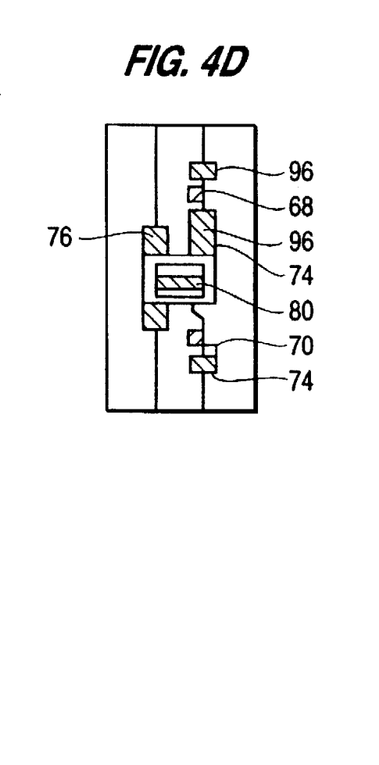
FIG. 4D shows the cross-section through the hydraulic actuator as indicated by the dashed line in FIG. 4B.
Figure 4E:
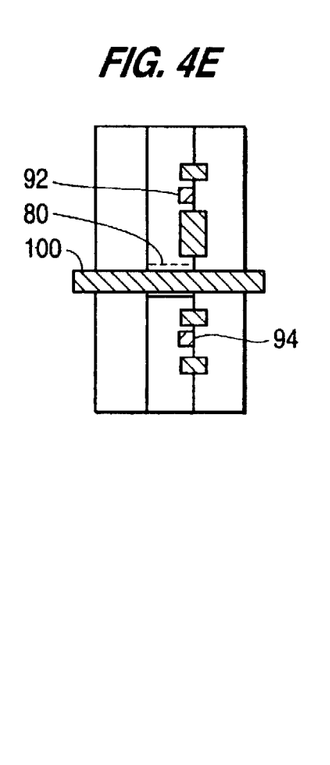
FIG. 4E shows the cross-section through the hydraulic actuator as indicated by the dashed line in FIG. 4B.
Figure 4F:
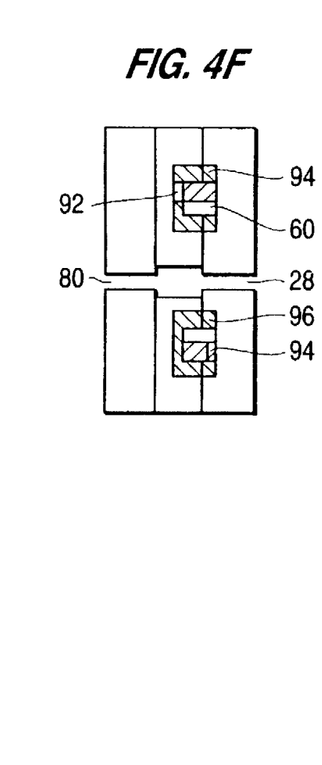
FIG. 4F shows the cross-section through the hydraulic actuator as indicated by the dashed line in FIG. 4B.

A gasket 96 lies in upper and lower gasket channels 72, 76 of middle plate 54 (FIG. 4C). It is seated partway below the surface of middle plate 54 and protrudes partly above. It includes a collar seal part (FIG. 4D) which rings piston shaft 84. The top, middle, and bottom plates are in a stack, with the piston inside. The slot 58 in the upper plate is aligned above guide slot 66. The piston shaft 84 and hole 88 are visible through it. The lower plate's slot 60 is aligned similarly. The gasket seats itself in the uppermost and lowermost gasket channels 74, 78 in the upper and lower plates respectively.

A pin 100 is inserted in hole 88 for transmitting the motion of the piston through the slots 58, 60 in the upper and lower plates.

EXAMPLE 1

The initial set-up of the surgical robot system, diagrammed in FIG. 1, is similar to the procedure used in laparoscopic surgery. Namely, a pneumoperitoneum is induced. A trocar is inserted through a small incision in the area of the navel, and a laparoscope 12 is inserted through the trocar. Trocars are also inserted one on either side of the laparascope, approximately six inches apart.

Once the laparoscope and trocars are in place, a surgical robot manipulator 20 is inserted in each of the second and third trocars. The manipulator is inserted into the trocar to a level partway up the forearm 30. The manipulator is positioned so the center of the work area, the abdominal wall incision, and the manipulator's base 24 lie along a line. Then, the manipulator base 24 is fixed in position using a clamp attached to the operating table.

The surgeon dons sensory gloves 16, and the microcomputer 18 is turned on. To use the manipulators to execute manual tasks, such as suturing, the surgeon moves his hands and fingers as if miming the action. The gloves sense the spatial positions of the surgeon's hands, as well as the flexion angles of his thumbs and index fingers. The information is transmitted to the computer, which then opens and closes valves as necessary to operate the hydraulic actuators. The hydraulic actuators move the joints in the manipulator so as to reproduce the surgeon's motions in real time. Thus, if the surgeon moves his left hand one centimeter left, the end effector of the left arm moves a centimeter left. If the surgeon brings his right thumb and index finger together, the jaws of the right end-effector close.

In FIG. 2, note that the elbow joint 26 has no actuators and thus moves freely. This feature allows the manipulator arm to pivot freely where it passes through the trocar and the abdominal wall. Since the patient lies essentially still during the operation, this point can be treated as fixed. The forearm 30 can slide in and out through this point, and can also pivot and rotate. Thus, the position of the end-effector can be controlled by the actuators of the shoulder 26 and wrist 32. The response of the elbow to shoulder movements (transmitted to the computer by the joint deflection sensors) allows the computer to calculate the relative position of the abdominal-wall pivot point. With this information, the computer can move the end-effector 34 along any desired path or to any desired point.

The end-effector 34 of FIG. 3 contains a miniature hydraulic actuator 40. In operation, the jaws may be opened or closed by supplying oil pressure to the inlet tubes 92, 94 (shown in FIG. 4). When pressure is supplied to first tube 92, it enters the outer oil flow channel 68 and flows to the left side of piston 80. This causes the piston to extend, pulling on the coupling 50, which rotates moveable jaw 48 counterclockwise. The jaws are closed in a similar manner when pressure is supplied to second tube 94.

In FIG. 4, note that ferrules 90 are preferably epoxy (3M #2216) and are molded directly onto tubes 92, 94. The tubes are preferably teflon, with $\frac{1}{32}$" O.D. and $\frac{1}{64}$" I.D. The tubes are initially treated with TetraEtch (W.L. Gore & Associates, Flagstaff, Ariz.) to bond the epoxy.

Note that gasket 96 is preferably formed by pouring silicone rubber (Dow Corning 3112 RTV Silicone) over the piston, as well as over the top, bottom, and middle plates, and then assembling the actuator. Piston rings 86 are formed simultaneously. When the silicone gasket cures, it forms a barrier around the oil flow channels, which prevents the oil from seeping out between the middle and top plates. The piston chamber is sealed in a similar manner, as are the inlet tubes 92, 94 in the oil flow channels 68, 70. The ferrules 90 prevent the inlet tubes from being inadvertently pulled out of the flow channels. Also, they may assist in sealing, since they interrupt the smooth walls of the tubes, along which hydraulic fluid might otherwise seep. The silicone forms a continuous collar around the piston shaft to prevent leakage there.

After the silicone has cured, upper plate 52 is removed and excess silicone is removed from piston chamber 64 and oil flow channels 68, 70. Fluid pumped into flexible tubes 92, 94 ejects any silicone that may have clogged them. Finally, upper plate 52 is replaced, and all three plates are joined permanently by means of solder or glue applied around the edges. In the case of solder, a low-temperature variety is preferred, so as to avoid damage to the silicone.

Arm Construction

To provide dexterity, the manipulator almost inevitably requires a complex structure. However, it must be inexpensive, since part or all of it is preferably disposable. To enable this, a shift of paradigm is employed. Specifically, the manipulator has a planar layered structure, much like an integrated circuit (microchip). Thus it can be produced by a simple process of laminating sheets of material. Each sheet has holes for rotary linkages, channels for hydraulic fluid, and slots for pistons. A complete manipulator can be produced in this way in a nearly-assembled state. Moreover, many manipulators can be produced simultaneously from a large sheet.

Actuator Construction

As with a conventional gasket or O-ring, pressure on the silicone gasket deforms it, and compresses it into the surrounding surfaces. The greater the pressure, the greater the sealing force. At low pressures, the compression of the silicone is decreased and friction, e.g. of the piston on the collar, is lessened. Note that in a conventional hydraulic cylinder, several seals must be individually fabricated and installed; in the miniature hydraulic actuator, all of the seals are simultaneously created in-situ, eliminating these fabrication and assembly steps. The piston rings function in an analogous manner. Note that even if the piston is undersize, the piston rings make a good seal. This is because they are molded in-situ. The process allows precise fabrication with imprecise methods. Note that the piston has a rectangular cross-section. It would be difficult to create an effective piston ring for such a piston using conventional means.

Note that the shaft of the piston slides in a guide slot in the middle plate. This design constrains the piston, preventing motion perpendicular to its intended travel. In conventional hydraulic cylinders, the piston shaft lacks such a guide, but fits into the cylinder very precisely, so as to prevent perpendicular motion. On the small scale, however, such precision is not achievable. Thus, side loads could induce significant displacement of the piston, causing it to jam or wear. This would be a particularly serious problem if parts were made of soft materials such as plastic. Using the constrained piston design, however, use of plastic is not a problem. Use of plastic in this application would be desirable, since plastic can be economically molded into small parts with complex shapes.

Thus, the robot of the present invention enhances the safety, economy, speed, and ease of laparoscopic surgery. Its advantages include:

(a) The sensory glove interface allows the user to employ natural eye-hand coordination in laparoscopic surgery, which is not possible using available products.

(b) A sensory glove is less expensive than a force-reflecting master, but retains many of its advantages.

(c) The unique hydraulic actuator will allow the surgical robot system to be manufactured simply and economically, despite the system's complexity. Its planar structure allows it to be integrated into complex systems including hydraulic interconnections, rotary and linear mechanical linkages, sensors, and electronics. All parts can be fabricated concurrently in one or two steps, using etching and molding techniques. The in-situ molded gasket reduces the need for precise fabrication, and also reduces the number of assembly steps.

Additional advantages of the present invention are that it provides:

(a) a laparoscopic surgical system with a natural user interface, implemented by means of a sensory glove;

(b) a master-slave type surgical system with a sensory glove control and miniature manipulators allowing access to the abdominal cavity through small incisions;

(c) a laparoscopic surgical instrument whose tip moves in the same direction as the surgeon's hand, preserving the surgeon's natural eye-hand coordination and thereby enhancing the speed, ease, and safety of laparoscopic surgery;

(d) a laparoscopic surgical manipulator with joints for added dexterity;

(e) a laparoscopic surgical manipulator with a wrist, to allow suture lines running any desired direction;

(f) a dextrous, robot-like surgical instrument which is inexpensive enough to be disposable;

(g) a hydraulic actuator with a layered planar structure, allowing economical high-volume production of complex robot-like devices, such as multi-fingered robot hands;

(h) a hydraulic actuator with a planar structure, facilitating miniaturization to a size below one centimeter;

(i) a miniature hydraulic actuator wherein the piston is constrained to prevent sideways motion, thus compensating for the inherent dimensional variation of small manufactured parts, which would otherwise lead to jamming of the piston, excessive wear, or hydraulic fluid leakage; and (j) a means of making seals which are small, dimensionally precise, and reliably prevent hydraulic fluid leakage.

While the invention has been described in detail and with reference to specific embodiments thereof, it will be apparent to one skilled in the art that various changes and modifications can be made therein without departing from the spirit and scope of the invention.

We claim:

1. A layered hydraulic actuator comprising a top plate, a middle plate, a bottom plate, a piston, and means for conducting hydraulic fluid;

wherein the middle plate comprises at least one chamber adapted to receive the piston and permit the piston to move up and down the length of the chamber;

wherein the means for conducting hydraulic fluid empties into the chamber housing the piston such that the piston is displaced up and down the length of the chamber when the hydraulic fluid flows into and out of the chamber; and wherein the top plate and the bottom plate are attached to the top and bottom, respectively, of the middle plate, thereby enclosing the chamber containing the piston.

2. An actuator according to claim 1, wherein the middle plate and bottom plate are combined as a single plate.

3. An actuator according to claim 1, wherein the piston comprises a head and a shaft and the middle plate comprises an edge, two chambers and at least one channel leading from the edge to the first chamber which comprises two ends and is adapted to receive the head of the piston and permit displacement of the piston head between the two ends of the first chamber; and wherein one end of the first chamber connects to a second chamber into which the shaft of the piston extends.

4. An actuator according to claim 3, wherein the actuator is no more than 3 centimeters in width and no more than 5 centimeters in length.

5. An actuator according to claim 4, which produces a force of at least 4 kilograms and a displacement of at least a half centimeter.

6. An actuator according to claim 1, wherein the chamber is coated with a sealant.

7. An actuator according to claim 1, wherein the piston is coated with a sealant that enables the piston to slide within the chamber with low friction.

8. A method of producing a layered hydraulic actuator comprising the steps of (a) forming top, bottom, and middle plates, wherein the middle plate has a cut-out first chamber and an adjoining second smaller chamber, (b) inserting a piston having a head and a shaft into the chambers of the middle plate such that it can slide back and forth within the chambers, the head of the piston being housed in the first chamber and the shaft being housed in the second chamber, (c) forming at least one channel in the middle plate to conduct hydraulic fluid into said first chamber, and (d) joining said lower, middle, and upper plates in a stacked arrangement, such that the first chamber of the middle plate is enclosed to form a cavity containing the piston.

9. A method according to claim 8, further comprising the steps of (e) coating the piston with a liquid, (f) inserting the piston into the first chamber, and (g) causing the liquid to solidify into a coating around the piston.

10. A method according to claim 8, further comprising the steps of (e) introducing a liquid into the first chamber after introducing the piston therein, and (f) causing said liquid to solidify into a coating around the piston.

11. A method according to claim 8, further comprising the steps of (e) forming a groove in each of said upper, middle, and lower plates which circumscribes said chambers and said at least one channel, (f) filling said grooves with a fluid, (g) assembling said actuator, and (h) causing said fluid to solidify, whereby the solidified fluid provides a seal to prevent leakage of hydraulic fluid conducted by said at least one channel.

12. A method according to claim 11, wherein the seal-forming fluid is castable rubber.

13. A method according to claim 8, further comprising the following steps which are performed prior to step (d) of claim 8:

providing grooves in the top and bottom plates which circumscribe the slots and channels of the middle plate and then introducing a gasket-forming liquid into said grooves.

14. A method according to claim 8, wherein, prior to step (b) of claim 8, the piston is coated with a sealant that permits the piston to slide within the piston chamber with low friction.

* * * * *